United States Patent
Trinkle et al.

(10) Patent No.: US 7,488,812 B2
(45) Date of Patent: Feb. 10, 2009

(54) CHITOSAN PRODUCTION

(75) Inventors: James R. Trinkle, Bussey, IA (US);
Ki-Oh Hwang, Cedar Rapids, IA (US);
Weiyu Fan, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 353 days.

(21) Appl. No.: 10/509,570

(22) PCT Filed: Apr. 2, 2003

(86) PCT No.: PCT/US03/10560

§ 371 (c)(1),
(2), (4) Date: Sep. 29, 2004

(87) PCT Pub. No.: WO03/086281

PCT Pub. Date: Oct. 23, 2003

(65) Prior Publication Data

US 2005/0215774 A1    Sep. 29, 2005

Related U.S. Application Data

(60) Provisional application No. 60/369,594, filed on Apr. 2, 2002.

(51) Int. Cl.
  *C08B 37/08*  (2006.01)
  *C07H 1/06*  (2006.01)
  *C07H 1/08*  (2006.01)

(52) U.S. Cl. .................................. 536/20; 536/127

(58) Field of Classification Search ............... None
See application file for complete search history.

(56) References Cited

U.S. PATENT DOCUMENTS

| | | | |
|---|---|---|---|
| 2,040,879 A | 5/1936 | Rigby | |
| 3,232,836 A | 2/1966 | Carlozzi et al. | |
| 3,632,754 A | 1/1972 | Balassa | |
| 3,903,268 A | 9/1975 | Balassa | |
| 3,911,116 A | 10/1975 | Balassa | |
| 3,914,413 A | 10/1975 | Balassa | |
| 4,056,432 A | 11/1977 | Slagel et al. | |
| 4,282,351 A | 8/1981 | Muzzarelli | |
| 4,806,474 A | 2/1989 | Hershberger | |
| 4,886,541 A | 12/1989 | Hadwiger | |
| 4,948,881 A | 8/1990 | Naggi et al. | |
| 4,970,150 A | 11/1990 | Yaku et al. | |
| 4,978,381 A | 12/1990 | Hadwiger | |
| 5,219,749 A | 6/1993 | Bouriotis et al. | |
| 5,232,842 A | 8/1993 | Park et al. | |
| 5,262,310 A | 11/1993 | Karube et al. | |
| 5,599,916 A * | 2/1997 | Dutkiewicz et al. | ............ 536/20 |
| 5,730,876 A | 3/1998 | You et al. | |
| 5,905,035 A | 5/1999 | Okada et al. | |
| 5,985,644 A | 11/1999 | Roseman et al. | |
| 5,998,173 A | 12/1999 | Haynes et al. | |
| 6,117,851 A | 9/2000 | Sherman et al. | |
| 6,333,399 B1 | 12/2001 | Teslenko et al. | |
| 2005/0245482 A1 | 11/2005 | Fan et al. | |

FOREIGN PATENT DOCUMENTS

| | | |
|---|---|---|
| EP | 0 400 364 A2 | 12/1990 |
| EP | 0885954 | 12/1998 |
| GB | 458839 | 12/1936 |
| JP | 55012109 A2 | 1/1980 |
| JP | 62070401 A2 | 3/1987 |
| JP | 63097633 A2 | 4/1988 |
| JP | 63225602 A2 | 9/1988 |
| JP | 2149335 A2 | 6/1990 |
| JP | 2180903 A2 | 7/1990 |
| JP | 2200196 A2 | 8/1990 |
| JP | 2229832 A2 | 9/1990 |
| JP | 2258740 A2 | 10/1990 |
| JP | 5068580 A2 | 10/1993 |
| JP | 7330808 A2 | 12/1995 |
| JP | 08-041106 | 2/1996 |
| JP | 10297913 A2 | 11/1998 |
| WO | WO 98/42755 | 10/1998 |
| WO | WO 00/04182 | 1/2000 |
| WO | WO0168714 A1 * | 9/2001 |

OTHER PUBLICATIONS

Hu, et al. "Rapid Extraction of High-Quality Chitosan From Mycella of Absida Glauca," Journal of Food Biochemistry 23 (1999) 187-196.*

Kondo et al. Biol. Pharm. Bull. 23(12) 1458-1464 (2000).*

Arcidiacono and Kaplan, "Molecular Weight Distribution of Chitosan Isolated from *Mucor rouxii* under Different Culture and Processing Conditions," *Biotechnol. Bioeng.* 39:281-286, 1992.

Aiba, S., "Preparation of N-acetylchitooligosaccharides from lysozymic hydrolysates of partially N-acetylated chitosans" *Carbohydrate Research*, vol. 261, pp. 297-306 (1994).

(Continued)

*Primary Examiner*—Shaojia Anna Jiang
*Assistant Examiner*—Layla Bland
(74) *Attorney, Agent, or Firm*—Klarquist Sparkman, LLP

(57) ABSTRACT

The invention provides a method of producing chitosan using pressures greater than 0 PSIG. The invention also provides fungal chitosan compositions.

15 Claims, 3 Drawing Sheets

OTHER PUBLICATIONS

Alonso, I., et al., "Determination of the Degree of Acetylation of Chitin and Chitosan by Thermal Analysis," *Journal of Thermal Analysis*, vol. 28, pp. 189-193 (1983).

Bartnicki-Garcia S., "Cell Wall Chemistry, Morphogenesis, and Taxonomy of Fungi," *Chemistry of Fungal Cell Wall*, pp. 87-108 (1968).

Benjakul, S. et al., "Improvement of Deacetylation of Chitin from Black Tiger Shrimp (*Penaeus monodon*) Carapace and Shell," *ASEAN Food Journal*, vol. 9, No. 4, pp. 136-140 (1994).

Beri, R. et al., Characterization of Chitosans via Coupled Size-Exclusion Chromatography and Multiple-Angle Laser Light-Scattering Technique, *Carbohydrate Research*, vol. 238, pp. 11-26 (1993).

Biermann, C., "Hydrolosis and Other Cleavage of Glycosidic Linkages," Chapter 3, pp. 29-41, date unknown.

Carlson, T. et al., "Chitin/Chitosan Extraction from *A. niger* Mycelium," *Cargill Central Research*, 16 pages (Aug. 1997).

"Chitin/Chitosan Specifications," *Biopolymer Engineering, Inc.*, http://www.biopolymer.com/spec.htm, 1 page (date printed Mar. 4, 1999).

Davies, D., et al., "Determination of the Degree of Acetylation of Chitin and Chitosan," *Methods in Enzymology*, vol. 161, Part B, pp. 442-446 (1988).

Domszy, J. et al., "Evaluation of Infrared Spectroscopic Techniques for Analysing Chitosan," *Makromal. Chem.*, vol. 186, pp. 1671-1677 (1985).

Farkas, V., et al., "Fungal Cell Walls: Their Structure, Biosynthesis and Biotechnological Aspects," *Acta Biotechnol.*, vol. 10, No. 3, pp. 225-238 (1990).

Fleet, G., et al., "17 Fungal Glucans—Structure and Metabolism," *Encyclopedia of Plant Physiology*, vol. 13B, New Series, pp. 416-440 (1981).

Gassner, G., et al., "Teichuronic Acid Reducing Terminal *N*-Acetylglucosamine Residue Linked by Phosphodiester to Peptidoglycan of *Micrococcus luteus*," *J. Bacteriol.*, vol. 172, No. 5, pp. 2273-2279 (May 1990).

Gobin, P., et al., "Structural Chemistry of Fungal Polysaccharides," pp. 367-417 (1968).

Johnston, I., "The Composition of the Cell Wall of *Asperigillus niger*", *Biochem J*, vol. 96, pp. 651-658 (1965).

Kurita, K., "Controlled Functionalization of the Polysaccharide Chitin," *Prog. Polym. Sci.*, vol. 26, pp. 1921-1971 (2001).

Kurita, K., et al., Studies on Chitin, 3, Preparation of Pure Chitin, Poly (*N*-acetyl-D-glucosamine), from the Water-Soluble Chitin, *Makromal. Chem.*, vol. 178, pp. 2595-2602 (1977).

Kurita, K, et al., "Studies on Chitin, 4, Evidence for Formation of Block and Random Copolymers of *N*-Acetyle-D-glucosamine and D-Glucosamine by Hetero- and Homogeneous Hydrolyses," *Makromol. Chem.*, vol. 178, pp. 3197-3202 (1977).

Mima, S., et al., "Highly Deacetylated Chitosan and Its Properties," *Journal of Applied Polymer Sciences*, vol. 28, pp. 1909-1917 (1983).

Maghami, G., et al., "Evaluation of the Viscometric Constants for Chitosan," *Makromol. Chem.*, vol. 189, pp. 195-200 (1988).

Muzzarelli, R., et al., Chelating, Film-Forming, and Coagulating Ability of the Chitosan-Glucan Complex from *Aspergillus niger* Industrial Wastes, *Biotechnology and Bioengineering*, vol. 22, pp. 885-896 (1980).

Nanjo, F., et al., "Enzymatic Method for Determination of the Degree of Deacetylation of Chitosan," *Analytical Biochemistry*, vol. 193, pp. 164-167 (1991).

Niola F., et al., "A Rapid Method for the Determination of the Degree of *N*-acetylation of chitin-chitosan samples by acid hydrolysis and HPLC," *Carbohydrate Research*, vol. 238, p. 1-9 (1993).

No, H., et al., "Preparation and Characterization of Chitin and Chitosan—A Review," *Journal of Aquatic Food Product Technology*, vol. 4, No. 2, pp. 27-52 (1995).

Novikov, V., et al., "Synthesis of D(+)-Glucosamine Hydrochloride," *Russian Journal of Applied Chemistry*, vol. 70, No. 9, pp. 1467-1470 (1997).

Ottoy, M., et al. "Preparative and Analytical Size-exclusion Chromatography of Chitosans," *Carbohydrate Polymers*, vol. 31, pp. 253-261 (1996).

Pelletier, A., et al., "Chitin/Chitosan Transformation by Thermo-Mechano-Chemical Treatment Including Characterization by Enzymatic Depolymerization," *Biotechnology and Bioengineering*, vol. 36, pp. 310-315 (1990).

Rege, P., et al., "Chitosan Processing: Influence of Process Parameters During Acidic and Alkaline Hydrolysis and Effect of the Processing Sequence on the Resultant Chitosan's Properties," *Carbohydrate Research*, vol. 321, Nos. 3-4, pp. 235-245 (Nov. 24, 1999).

Roberts, G., et al., "Determination of the Viscomtric Constants for Chitosan," *Int. J. Biol. Macromol.*, vol. 4, pp. 374-377 (Oct. 1982).

Rokem J., et al., "Degradation of Fungal Cell Walls Taking into Consideration the Polysaccharide Composition," *Enzyme Microb. Technol.*, vol. 8, No. 10, pp. 588-592 (Oct. 1986) (Abstract).

Ruiz-Herrera J., "Chemical Components of the Cell Wall of *Aspergillus* Species," *Archives of Biochemistry and Biophysics*, vol. 122, pp. 118-125 (1967).

Sabnis, S., et al., "Improved Infrared Spectroscopic Method for the Analysis of *N*-deacetylation of Chitosan," *Polymer Bulletin*, vol. 39, pp. 67-71 (1997).

Sannan, T., et al., "Studies on Chitin, 2, Effect of Deacetylation on Solubility," *Makromol. Chem.*, vol. 177, pp. 3589-3600 (1976).

Shahidi, F., et al., "Food Applications of Chitin and Chitosans," *Trends in Food Science & Technology*, vol. 10, pp. 37-51 (1999).

Stagg, C., et al., The Characterization of a Chitin-Associated D-Glucan from the Cell Walls of *Aspergillis niger*, *Biochim. Biophys. Acta*, vol. 320, pp. 64-72 (1973).

Stainer, R., et al., "The Microbial World," *Prentice-Hall, Inc.*, pp. 332-336 (1970).

Tan, S., et al., The Degree of Deacetylation of Chitosan: Advocating the First Derivate UV-spectrophotometry Method of Determination, *Talanta*, vol. 45, pp. 713-719 (1998).

Wessels, J., et al., "15 Fungal Cell Walls: A Survey," *Plant Carbohydrates II, Extracellular Carbohydrates*, pp. 352-394 (1981).

Wu, A., et al., "Determination of Molecular-Weight Distribution of Chitosan by High-performance Liquid Chromatography," *Journal of Chromatography*, vol. 128, pp. 87-99 (1976).

Xin et al., "Primary Study on the Production of Chitosan by the Method of Cutluring Microorganism," Food Science, p. 22 (3 pp.), Jul. 1997 (partial English translation).

G. Kogan, "(1→3,1→6)-β-D-Glucans of Yeasts and Fungi and Their Biological Activity," *Studies in Natural Products Chemistry*, 23:107-152, 2000.

Muzzarelli et al., "Chitosan from *Absidia coerulea*," *Carbohydrate Polymers*, 25:45-50, 1994.

No et al., "Effective Deacetylation of Chitin Under Conditions of 15 psi/121° C.," *J. Agric. Food Chem.*, 48:2625-2627, 2000.

\* cited by examiner

CHITOSAN PRODUCTION

CROSS REFERENCE TO RELATED APPLICATIONS

This is the U.S. national stage of PCT/US03/10560 filed Apr. 2, 2003, which claims priority to U.S. provisional application No. 60/369,594, filed Apr. 2, 2002, which is herein incorporated by reference.

FIELD OF THE INVENTION

The invention relates to producing chitosan.

BACKGROUND

Chitosan is a deacetylated form of chitin. Chitin is a polysaccharide that is found in the shells of insects, crustaceans, mollusks, and fungal biomass. Chitosan has been identified as having various uses, for example as a binder in paper making, a component in bandages, and as a wound healing compound.

The quality of chitosan varies with the degree of deacetylation of the N-acetyl groups, molecular weight, purity, manufacturing process, color, clarity, consistency, and uniformity.

SUMMARY

The invention provides a method for producing fungal chitosan from chitin-containing material using greater than 0 PSIG (pounds per square inch gauge). This method allows for the production of chitosan with increased deacetylation levels and increased molecular weight compared to similar processes that do not use increased pressure. Similarly, the invention provides chitosan that has greater purity increased molecular weight, and increased deacetylation compared to processes that do not use increased pressure. Because the invention provides a method for producing high purity fungal chitosan from chitin-containing material it is not necessary to take additional steps to purify the chitosan. However, if the desired product requires utilization of reaction parameters that do not yield high purity it may be desirable to separate the chitosan from the reaction. Separation can be accomplished using any method known in the art, i.e filtration, centrifugation, etc.

Another aspect of the invention provides compositions made by the method.

In yet another aspect the invention provides fungal chitosan compositions that are characterized by their combination of increased molecular weight and increased deacetylation levels, as well as compositions characterized by their combination of increased deacetylation levels, increased molecular weight and increased purity.

DETAILED DESCRIPTION

Fungal Biomass

Figure 1:
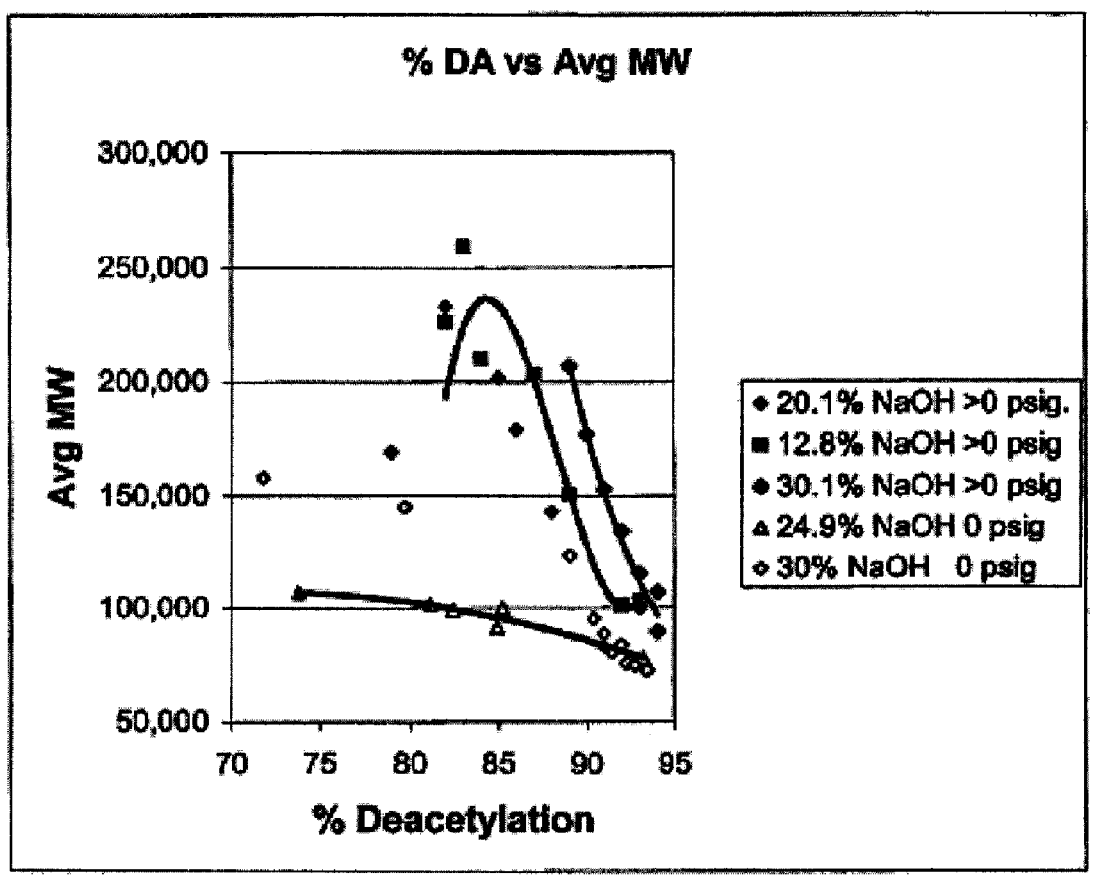
FIG. 1 is a graph showing a comparison of the average molecular weight to the percent deacetylation.
Figure 2:
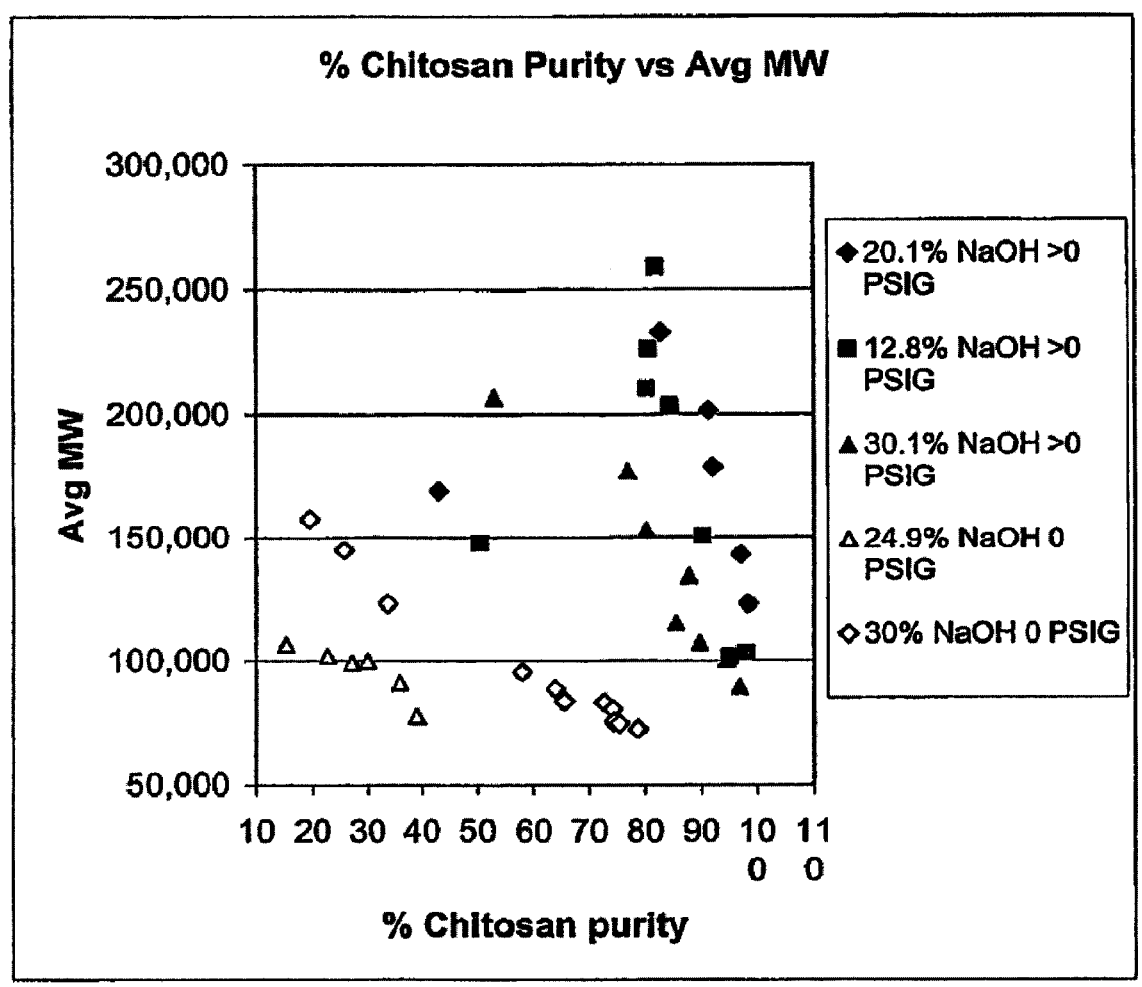
FIG. 2 is a graph showing a comparison of the average molecular weight to the percent purity of chitosan.
Figure 3:
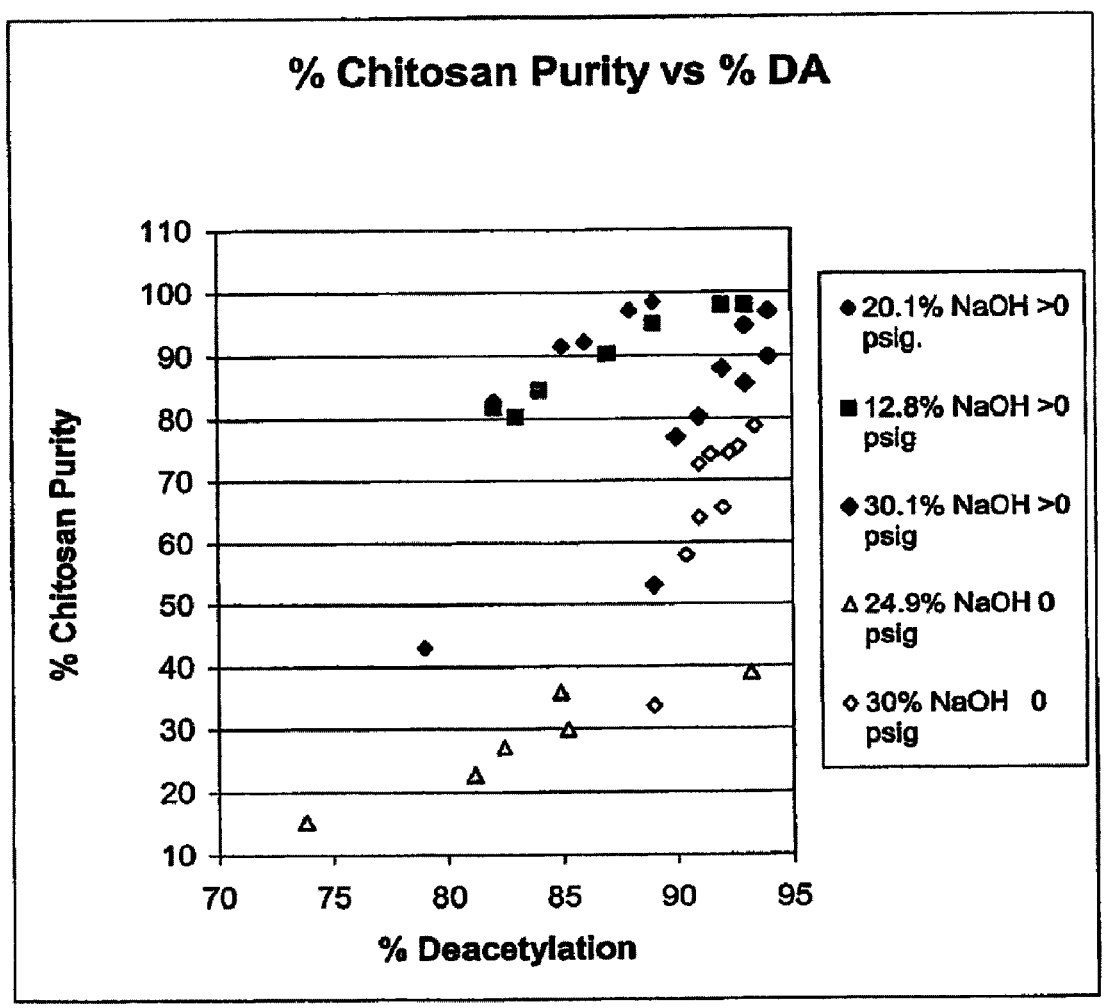
FIG. 3 is a graph showing a comparison of the percent purity of the chitosan to the percent deacetylation of the chitosan.

Chitosan described herein is prepared from chitin contained in fungal biomass. Suitable sources of fungal biomass include, for example, *Aspergillus niger, Aspergillus terreus, Aspergillus oryzae, Candida guillermondii, Mucor rouxii, Penicillium chrysogenum*, and *Penicillium notatum*.

Fungal biomass usually has between 5 and 25 percent chitin, and typically from 10 to 20 percent chitin, based upon dry weight of the biomass. Particularly useful sources of fungal biomass are commercial fermentation processes such as those used to make organic acids, such as citric acid.

Caustic

Caustic material can be used either in the reaction directly or in an aqueous solution. Examples of caustic material that can be used in the reaction include, sodium hydroxide, potassium hydroxide, calcium hydroxide, caustic alcohol, or other alkalis. Any concentration of caustic can be used provided that the caustic reacts with the other components of the reaction to yield chitosan. Generally, caustic is used at a concentration from about 5% to about 40% by weight, and more specifically from about 15% to about 30% by weight.

Reaction Conditions

The reaction that causes the production of chitosan from fungal biomass and/or chitin from fungal biomass (hereinafter collectively referred to as chitin-containing material), involves reacting the caustic material with the chitin-containing material at a pressure greater than atmospheric pressure. The temperature, time of reaction, and pressure that are used to form chitosan will vary depending on the desired deacetylation level and the desired molecular weight of the chitosan.

Any temperature that will produce the desired chitosan product can be used. However, temperatures from about 80° C. to about 150° C. and more specifically, temperatures greater than 90° C., 100° C., 115° C., 125° C., 130° C., and 140° C can be used to produce the chitosan.

The reaction can be carried out for any length of time that will produce the desired chitosan product. However, typical reactions times vary from about 1 hour to about 50 hours and more specifically, reaction times greater than 4, 6, 10, 15, 20, 25, and 30 hours are preferred.

Any pressure that is greater than 0 PSIG can be used to produce the chitosan. Generally, pressures greater than 1, 2, 3, 5, 10, 15, or 20 PSIG are used. The pressure can be increased to the theoretical maximum pressure, which depends on the temperature, solubility of the caustic, and the concentration of other reactants in the solution.

Pressure can be applied by using any method known to those of ordinary skill in the art. For example, pressure in the reacting vessel can come from increased vapor pressure due to higher temperatures achieved in a closed vessel, or can come from an external force applied to the vessel contents. Increasing the temperature to 130° C., in a closed vessel containing water, will increase the pressure in that vessel to approximately 15 PSIG. Another way to increase the pressure would be to maintain temperature at a constant level, and apply an outside source of pressure, by reducing the volume of the container, or attaching an outside gas source to raise the pressure to the desired level. This outside source could be an inert gas such as nitrogen, helium or ammonium from a pressurized tank.

Fungal Chitosan

The compositions of the invention are characterized by their combination of high deacetylation levels and high molecular weights. Compositions of the invention can have deacetylation levels greater than 85%, 90%, and 95%. Similarly, compositions of the invention can have molecular weights greater than 80,000, 90,000, 100,000, 150,000, and 175,000.

In other embodiments compositions of the invention can be characterized by their purity level. For example fungal chitosan composition having purity levels of greater than 85%, 90%, and 95% can be obtained.

EXAMPLES

The following examples are provided to demonstrate production of fIngal chitosan from a chitin containing material. In the examples depicted, the chitosan was produced under pilot laboratory conditions. However, the invention is also applicable to production of chitosan in large-scale manufacturing operations, particularly where uniform sources of fungal biomass are available.

Example 1

Method of Obtaining and Purifying Chitosan from Fungal Biomass using 20.1% NaOH at Greater than 0 PSIG 29.9 kg of fungal biomass (*Aspergillus niger*) at 17.14% dry solids, 21 liters of 50% NaOH, and 18 liters of water were added to a pressure reactor which was made using materials available on site. However, commercial models such as, for example, the Miniclave Pressure Reactor from CTP Corporation, Northport, N.Y., can also be used to give the results provided herein. This resulted in a final ratio in the mixture of 6.0% dry biomass, 20.1% NaOH, and 73.9% water. This alkali biomass solution was heated using a steam coil to approximately 130° C. and held in the sealed reactor for 28 hours. Since this was above the boiling point of 20% caustic (109° C.), 14-16 PSIG pressure was contained in the reactor, as well as the ammonia and other gases released in the associated reactions.

Samples were taken periodically. The samples were filtered and washed with water to remove the NaOH, salts and other soluble by-products. The filtered solids contained the chitosan-containing material, made up primarily of chitosan and glucans. The chitosan was then separated from the glucans by dissolving the filtered solids in acetic acid (pH 4.0), and centrifuging to separate the insoluble glucans from the soluble chitosan.

The amount of chitosan was measured and the percent chitosan in the filtered solids was calculated to provide a % purity on a dry weight basis. The average molecular weight of the chitosan was measured by a size exclusion column (SEC) on chitosan that had been separated from the chitosan containing-material by acidifying with acetic acid and centrifugation.

First derivative ultraviolet spectrophotometry was used for measuring the degree of deacetylation of chitosan was first derivative ultraviolet spectrophotometry. This was described by Riccardo A. A. Muzzarelli and Roberto Rocchetti, Determination of the Degree of Acetylation of Chitosans by First Derivative Ultraviolet Spectrophotometry, Carbohydrate Polymers, 5:461-472, 1985.

The results of this example are in Table 1.

Example 2

Method of Obtaining and Purifying Chitosan from Fungal Biomass using 12.8% NaOH at Greater than 0 PSIG 40.8 kg of fungal biomass (*Aspergillus niger*) at 13.68% dry solids, 11 liters of 50% NaOH, and 12 liters of water were added to a pressure reactor. This gave a final ratio in the mixture of 8.0% dry biomass, 12.8% NaOH, and 79.9% water. This alkali biomass solution was heated using a steam coil to approximately 130° C. and held in the sealed reactor for 45 hours. Since this was above the boiling point of 12% caustic (104° C.), 18-20 PSIG pressure was contained in the reactor, as well as the ammonia and other gases released in the associated reactions.

Samples were taken periodically. The samples were filtered and washed with water to remove the NaOH, salts and other soluble by-products. The filtered solids contained the chitosan-containing material, made up primarily of chitosan and glucans. The chitosan was then separated from the glucans by dissolving the filtered solids in acetic acid (pH 4.0), and centrifuging the insoluble glucans from the soluble chitosan.

Measurements were made in a similar manner to those described in Example 1.

The results of this Example are in Table 2.

Example 3

Method of Obtaining and Purifying Chitosan from Fungal Biomass using 30.1% NaOH at Greater than 0 PSIG Chitosan was obtained and purified from *Aspergillus niger* using 30.1% NaOH. Other than a different caustic level, the conditions and processing steps are similar to those used in Example 2.

The results of this Example are shown in Table 3.

Example 4

Method of Obtaining and Purifying Chitosan from Fungal Biomass using 24.9% NaOH at 0 PSIG 208.6 kg *Aspergillus Niger* mycelium of which 18% was dry matter was mixed with 135 L of 50% NaOH to make a mixture that contained 24.9% NaOH and 8.9% solids. The mixture was heated to 110° C. for the time periods indicated in Table 4, below. Analysis of products are reported in Table 4.

Example 5

Method of Obtaining and Purifying Chitosan from Fungal Biomass using 30% NaOH at 0 PSIG 254 kg *Aspergillus Niger* mycelium of which 18% was dry matter was mixed with 250 L of 50% NaOH to make a mixture that contained 30% and 7% solids. The mixture was heated to 118° C. for the time periods indicated in Table 5, below. Analysis of products are reported in Table 5.

TABLE 1

20.1% NaOH

| Time (hr) | Temp (C.) | Pressure (PSIG) | Average Molecular Weight of Chitosan | Average Molecular Number of Chitosan | % DA of Chitosan | Chitosan Purity in dry cake |
|---|---|---|---|---|---|---|
| 4 | 130 | 14 | 169,104 | 48,350 | 79 | 43.0 |
| 12 | 132 | 14 | 232,964 | 45,637 | 82 | 82.8 |
| 16 | 130 | 16 | 201,681 | 41,401 | 85 | 91.4 |
| 20 | 132 | 14 | 178,736 | 37,254 | 86 | 92.1 |
| 24 | 129 | 14 | 142,814 | 33,144 | 88 | 97.1 |
| 28 | 130 | 14 | 122,975 | 28,540 | 89 | 98.4 |

PSIG* pounds per square inch gauge
Cake* refers to the dry solids remaining after the reaction
% DA* refers to percent deacetylation

TABLE 2

12.8% NaOH

| Time (hr) | Temp (C.) | Pressure (PSIG) | Average Molecular Weight of Chitosan | Average Molecular Number of Chitosan | % DA of Chitosan | Chitosan Purity in dry cake |
|---|---|---|---|---|---|---|
| 6 | 130 | 14 | 147,574 | 38,236 | 83 | 50.5 |
| 12 | 128 | 13 | 226,316 | 38,349 | 82 | 80.6 |
| 15 | 130 | 15 | 258,933 | 38,428 | 83 | 81.9 |
| 18 | 128 | 15 | 210,449 | 34,844 | 84 | 80.3 |
| 24 | 128 | 14 | 203,543 | 33,856 | 87 | 84.5 |
| 30 | 130 | 15 | 150,629 | 26,669 | 89 | 90.3 |
| 40 | 130 | 15 | 101,464 | 23,253 | 92 | 95.0 |
| 42 | 130 | 15 | 103,143 | 23,624 | 93 | 97.9 |
| 45 | 130 | 15 | 103,143 | 23,624 | 93 | 97.9 |

TABLE 3

30.1% NaOH

| Time (hr) | Temp (C.) | Pressure (PSIG) | Average Molecular Weight of Chitosan | Average Molecular Number of Chitosan | % DA of Chitosan | Chitosan Purity in dry cake |
|---|---|---|---|---|---|---|
| 2 | 131 | 14 | 206,647 | 61,876 | 89 | 53.0 |
| 4 | 135 | 11 | 176,844 | 50,253 | 90 | 76.9 |
| 6 | 133 | 10 | 152,997 | 42,720 | 91 | 80.2 |
| 8 | 133 | 10 | 134,026 | 38,885 | 92 | 87.8 |
| 10 | 132 | 13 | 115,210 | 34,949 | 93 | 85.5 |
| 12 | 132 | 11 | 107,080 | 32,099 | 94 | 89.7 |
| 14 | 132 | 10 | 100,386 | 29,954 | 93 | 94.6 |
| 16 | 132 | 10 | 89,452 | 29,416 | 94 | 96.9 |

TABLE 4

0 PSIG
24.9% NaOH

| Time (hr) | Temp (C.) | Average Molecular Weight of Chitosan | Average Molecular Number of Chitosan | % DA of Chitosan | Chitosan Purity in dry cake |
|---|---|---|---|---|---|
| 3 | 109 | 106,615 | 44,690 | 73.8 | 15.3% |
| 4 | 108 | 101,681 | 43,523 | 81.1 | 22.7% |
| 6 | 108 | 99,004 | 42,855 | 82.4 | 27.1% |
| 7 | 108 | 99,850 | 40,977 | 85.2 | 29.9% |
| 8 | 112 | 91,112 | 39,815 | 84.9 | 35.9% |
| 24 | 111 | 77,626 | 32,463 | 93.2 | 39.0% |

TABLE 5

0 PSIG
30% NaOH

| Time (hr) | Temp (C.) | Average Molecular Weight of Chitosan | Average Molecular Number of Chitosan | % DA of Chitosan | Chitosan Purity in dry cake |
|---|---|---|---|---|---|
| 2 | 85 | 157770 | 81506 | 71.8 | 19.5% |
| 4 | 105 | 144843 | 70204 | 79.7 | 25.8% |
| 7 | 115 | 123054 | 58453 | 89.0 | 33.7% |
| 12 | 119 | 95370 | 42371 | 90.4 | 57.9% |
| 14 | 119 | 88609 | 39735 | 91.0 | 64.0% |
| 16 | 117 | 83685 | 37011 | 92.0 | 65.6% |
| 18 | 114 | 83104 | 35751 | 91.0 | 72.6% |
| 20 | 115 | 80494 | 35611 | 91.5 | 74.2% |
| 22 | 115 | 75438 | 32930 | 92.3 | 74.4% |
| 24 | 117 | 74664 | 31919 | 92.7 | 75.4% |
| 26 | 115 | 72383 | 31153 | 93.4 | 78.7% |

The results provided above show that at pressures greater than 0 PSIG the molecular weight of chitosan is greater at a specific deacetylation level when compared with chitosan made at 0 PSIG at the same deacetylation level. Furthermore, it is expected that by maintaining constant pressure on the reaction, greater temperatures can be used while not depolymerizing the chitosan.

Graph 1 provided below presents a comparison of the average molecular weight to the percent deacetylation from Tables 1 through 5 above. The open symbols represent data collected at 0 PSIG, and the solid symbols represent data collected at pressures greater than 0 PSIG.

The results provided above also show that at pressures greater than 0 PSIG the molecular weight of chitosan is greater at a specific purity level when compared with chitosan made at 0 PSIG at the same purity level.

Graph 2 provided below presents a comparison of the average molecular weight to the percent purity of the chitosan from Tables 1 through 5 above. The open symbols represent data collected at 0 PSIG, and the solid symbols represent data collected a pressures greater than 0 PSIG.

The results provided above also show that at pressures greater than 0 PSIG the average molecular weight is greater at higher percent purity of chitosan level when compared with chitosan made at 0 PSIG at the same purity level.

Graph 3 provided below presents a comparison of the percent purity of the chitosan to the percent deacetylation of the chitosan from Tables 1 through 5 above. The open symbols represent data collected at 0 PSIG, and the solid symbols represent data collected a pressures greater than 0 PSIG.

The results provided above also show that at pressures greater than 0 PSIG the percent purity of chitosan is greater at a specific percent deacetylation level when compared with chitosan made at 0 PSIG at the same purity level.

Having illustrated and described the principles of the invention in multiple embodiments and examples, it should be apparent to those skilled in the art that the invention can be modified in arrangement and detail without departing from such principles. We claim all modifications coming within the spirit and scope of the following claims.

What is claimed is:

1. A method for producing chitosan from fungal biomass, comprising:
   reacting the fungal biomass with a caustic at a pressure greater than 0 PSIG for at least 4 hours, thereby producing chitosan, wherein the average molecular weight of the chitosan is greater than 80,000 and less than about 258,933.

2. The method according to claim 1, further comprising separating the chitosan from the reaction.

3. The method according to claim 1, wherein the pressure is greater than 5 psig.

4. The method according to claim 1, wherein the pressure is greater than 10 psig.

5. The method according to claim 1, wherein the temperature is greater than 115° C.

6. The method according to claim 1, wherein the temperature is greater than 125° C.

7. The method according to claim 1, wherein the reaction occurs for greater than 15 hours.

8. The method according to claim 1, wherein the caustic is 5% to 40% by weight percent.

9. The method according to claim 1, wherein the caustic is 15% to 30% by weight percent.

10. The method according to claim 1, wherein the reaction occurs for greater than 6 hours.

11. The method according to claim 1, wherein the reaction occurs for greater than 10 hours.

12. The method according to claim 1, wherein the pressure is greater than 15 PSIG.

13. The method according to claim 1, wherein the pressure is greater than 20 PSIG.

14. A method for producing chitosan from fungal biomass, comprising:
    reacting the fungal biomass with a caustic at a pressure greater than 0 PSIG at a temperature greater than 125° C. for at least 12 hours, thereby producing chitosan, wherein the average molecular weight of the chitosan is greater than 80,000 and less than about 258,933.

15. The method according to claim 1, wherein the fungal biomass is *Aspergillus* biomass.

* * * * *